(12) United States Patent
Renner et al.

(10) Patent No.: US 10,743,931 B2
(45) Date of Patent: Aug. 18, 2020

(54) JAW ASSEMBLIES HAVING ELECTRICALLY ISOLATED JAWS AND CONSISTENT SPACING BETWEEN THE JAWS AT FULL CLOSURE

(71) Applicant: Ethicon LLC, Guaynabo, PR (US)

(72) Inventors: Ellen Renner, Cincinnati, OH (US); Kris Kallenberger, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 578 days.

(21) Appl. No.: 15/468,628

(22) Filed: Mar. 24, 2017

(65) Prior Publication Data

US 2018/0271586 A1 Sep. 27, 2018

(51) Int. Cl.
*A61B 18/14* (2006.01)
*A61B 90/00* (2016.01)
*A61B 17/29* (2006.01)
*A61B 18/00* (2006.01)

(52) U.S. Cl.
CPC ...... *A61B 18/1445* (2013.01); *A61B 18/1442* (2013.01); *A61B 2017/2926* (2013.01); *A61B 2018/0063* (2013.01); *A61B 2018/00083* (2013.01); *A61B 2018/1455* (2013.01); *A61B 2090/034* (2016.02)

(58) Field of Classification Search
CPC .... A61B 2017/2926; A61B 2018/0063; A61B 2018/145; A61B 2018/1452; A61B 2018/1455; A61B 2018/1457; A61B 2018/146; A61B 2018/1462; A61B 18/1442; A61B 18/1445; A61B 18/1447; A61B 2090/033; A61B 2090/034
See application file for complete search history.

(56) References Cited

U.S. PATENT DOCUMENTS 5,891,142 A * 4/1999 Eggers ............... A61B 18/1442
606/51
9,161,803 B2 10/2015 Yates et al.
(Continued)

FOREIGN PATENT DOCUMENTS

WO WO2002080796 A1 10/2002

*Primary Examiner* — Ronald Hupczey, Jr.
*Assistant Examiner* — Bradford C. Blaise
(74) *Attorney, Agent, or Firm* — Mintz Levin Cohn Ferris Glovsky and Popeo, P.C.

(57) ABSTRACT

Surgical access devices are provided having jaw assemblies that maintain a uniform spacing between the jaws and are electrically isolated from each other in a closed configuration. The devices provided for generally include one or more electrically insulative stops associated with a tissue engaging surface of one of the jaws, with the stops being configured to engage the tissue engaging surface of the opposed jaw. The stops set a uniform spacing between the jaws in the closed configuration, and provide electrical isolation. The stops can be disposed in intermediate, proximal, and/or distal portions of the jaw(s), and can be disposed at multiple locations of the jaw(s). The stops can come in many different forms and can be associated with jaws using a variety of techniques. Further, other embodiments, as well as methods for clamping tissue by providing a uniform gap between jaws during each closure stroke, are also provided.

17 Claims, 6 Drawing Sheets

(56) References Cited

U.S. PATENT DOCUMENTS

| | | | |
|---|---|---|---|
| 2004/0122423 A1* | 6/2004 | Dycus | A61B 18/1482 606/51 |
| 2005/0021027 A1* | 1/2005 | Shields | A61B 18/1445 606/51 |
| 2006/0224158 A1* | 10/2006 | Odom | A61B 18/1445 606/51 |
| 2011/0319882 A1* | 12/2011 | Kennedy | A61B 18/1445 606/33 |
| 2012/0078139 A1 | 3/2012 | Aldridge et al. | |
| 2013/0071282 A1* | 3/2013 | Fry | B22F 3/225 419/8 |
| 2013/0079774 A1* | 3/2013 | Whitney | A61B 18/1445 606/52 |
| 2014/0025073 A1* | 1/2014 | Twomey | A61B 18/1442 606/51 |
| 2015/0174390 A1 | 6/2015 | Nobis et al. | |
| 2015/0190191 A1 | 7/2015 | Strobl | |
| 2015/0209573 A1 | 7/2015 | Hibner et al. | |
| 2015/0272606 A1 | 10/2015 | Nobis | |

\* cited by examiner

JAW ASSEMBLIES HAVING ELECTRICALLY ISOLATED JAWS AND CONSISTENT SPACING BETWEEN THE JAWS AT FULL CLOSURE

FIELD

The present disclosure relates to surgical devices and methods for sealing or transecting tissue, and more particularly to improved features to electrically isolate jaws of a device and maintain a gap between the jaws in a closed configuration.

BACKGROUND

Surgical devices are used in various open, endoscopic, and laparoscopic surgeries to seal and/or transect tissue volumes and blood vessels. Devices used for sealing generally include jaws for grasping tissue therebetween and a cutting mechanism that is advanced through the grasped tissue to transect it. In some instances the devices can also be used to seal tissue volumes and blood vessels being transected, for instance by applying electrical energy to the grasped tissue to seal it before tissue transection is completed. For example, various mono-polar and bi-polar radio frequency (RF) surgical instruments and surgical techniques have been developed for sealing tissue volumes and blood vessels. Electrodes can be disposed on a face of one or both of the jaws and can apply energy to the grasped tissue to promote hemostasis.

One issue that can plague electrosurgical cutting devices is that tissue volumes and blood vessels being sealed may become damaged. When operating a tissue compression device, an amount of compression applied by the jaws to the tissue affects hemostasis. By increasing the amount of compression applied to the target tissue, the flow of blood can be limited, which can decrease the time necessary to achieve hemostasis. However, applying too much compression to manipulate tissue without sealing the tissue can result in damage to the tissue. The tissue is grasped and sealed by jaws of a surgical device having an electrode disposed in one or both of the jaws. Because an optimal amount of force depends on various factors, including the type and thickness of tissue disposed between the jaws, overcompression may result. Overcompression can make it difficult to apply resistive heating to tissue using an RF tissue sealing device and may result in a greater than desired contact area of the jaws with the grasped tissue. This increased contact area may cause undesired burning or charring of the tissue. Additionally, the inability to electrically isolate the electrode from the remaining jaw results in unwanted erosion of insulator material on the contact surface of the opposite jaw or an interruption of the electrical energy to the tissue. Higher compression settings move the jaws closer towards one another, causing parts of the electrode to directly contact the surface of the opposite jaw, possibly eroding the insulator material located thereon.

Accordingly, there remains a need for improved devices and methods that consistently and precisely set the gap between the jaws of the surgical device so as to avoid damage to the device, to the tissues being grasped and sealed when the device is in use, and ensure that the electrodes do not make contact with each other and short the device.

SUMMARY

Surgical access devices having jaw assemblies that maintain a uniform spacing between the jaws in a closed configuration are provided for in the present disclosure. Further, the jaw assemblies also include jaws that are electrically isolated from each other. Generally, at least one of the jaws includes one or more electrically insulative stops associated with its tissue engaging surface, with the stops being configured to engage the opposed tissue engaging surface of the opposed jaw. The stops both help set a uniform spacing between the jaws in the closed configuration, and provide the electrical isolation. The stops can be disposed in proximal and/or distal portions of the jaw(s), and in some exemplary embodiments are found in both the proximal and distal portions of the jaw(s). They can also be disposed in an intermediate portion of the jaw(s). Load can be more evenly distributed, for example, by providing multiple stops on a proximal portion of one of the jaws, the stops being opposed across a central longitudinal axis extending through a length of that jaw. This can likewise be done in lieu of or in addition to the proximal portion at the intermediate and/or the distal portions of the jaw(s). The stops can be associated with jaws using a variety of techniques, including but not limited to the techniques described herein. Further, the stops can come in many different forms, including but not limited to glass beads and/or ceramic beads.

In one exemplary embodiment, a surgical device includes a second jaw pivotally coupled to a first jaw, with each jaw having a tissue engaging surface such that a second tissue engaging surface of the second jaw is opposed to a first tissue engaging surface of the first jaw. The first tissue engaging surface of the first jaw includes an electrode. At least one of the jaws includes one or more electrically insulative stops. For example, in some exemplary embodiments, the second jaw includes one or more electrically insulative stops. In such an instance, the second jaw can include a first bore formed in a distal portion of the jaw and a second bore formed in a proximal portion of the jaw. Each of the first and second bores extend from the second tissue engaging surface and toward an outer surface of the second jaw that is opposed to the second tissue engaging surface. Further, a first electrically insulative stop is disposed in the first bore and a second electrically insulative stop is disposed in the second bore such that a portion of each of the first and second electrically insulative stops protrudes from the second tissue engaging surface. The first and second electrically insulative stops are configured to maintain the first tissue engaging surface at a consistent distance away from the second tissue engaging surface whenever the first and second jaws are in a fully compressed configuration, with the fully compressed configuration being a configuration in which at least one of the first and second jaws applies a force to the respective first or second tissue engaging surface of the other for the first and second jaws. Further, in the fully compressed configuration, the second jaw is electrically isolated from the electrode of the first jaw.

In some embodiments, a third electrically insulative stop can be disposed in a third bore formed in the proximal portion of the second jaw such that a portion of the third electrically insulative stop protrudes from the second tissue engaging surface. The third bore, like the first and second bores, can extend from the second tissue engaging surface and toward the outer surface of the second jaw. In such embodiments the second bore and the second electrically insulative stop can be disposed on one side of a central longitudinal axis of the second jaw and the third bore and the third electrically insulative stop can be disposed on an opposite side of the central longitudinal axis of the second jaw. Further, the second and third electrically insulative stops can be aligned such that a horizontal axis extending between centers of the second and third electrically insulative stops is approximately perpendicular to the central longitudinal axis of the second jaw.

At least one of the first and second bores can extend from the second tissue engaging surface to the outer surface of the second jaw, with a diameter of the bore proximate to the second tissue engaging surface being less than the diameter of the same bore located proximate to the outer surface.

The respective first or second electrically insulative stop that is disposed in at least one of the first and second bores can be a bead having a central diameter that is greater than the diameter of the bore in which it is disposed at the second tissue engaging surface and less than the diameter of the same bore at the outer surface. This allows the bead to pass through the bore from the outer surface and towards the second tissue engaging surface. The device can then include filler disposed in the bore to apply force to the bead in a direction toward the second tissue engaging surface to maintain a location of the bead with respect to the second tissue engaging surface.

In some embodiments both the first and second bores extend from the second tissue engaging surface to the outer surface of the second jaw, with a diameter of each bore proximate to the second tissue engaging surface being less than a diameter of the same bore located proximate to the outer surface. In some such embodiments, the first electrically insulative stop can be a first bead having a central diameter that is greater than the diameter of the first bore at the second tissue engaging surface and less than the diameter of the first bore at the outer surface. Likewise, the second electrically insulative stop can be a second bead having a central diameter that is greater than the diameter of the second bore at the second tissue engaging surface and less than the diameter of the second bore at the outer surface. The device can further include first and second filler, with the filler being used with the respective first and second beads. More particularly, the first filler can be disposed in the first bore and the second filler can be disposed in the second bore. Each of the first and second fillers can apply force to the respective first and second beads in a direction toward the second tissue engaging surface to maintain a location of the respective bead with respect to the second tissue engaging surface.

While in some instances the first and second bores extend through an entire thickness of the second jaw (i.e., from the second tissue engaging surface and through to the outer surface of the second jaw that is opposed to the second tissue engaging surface), in other instances one or both of the bores may not extend through the entire thickness. For example, at least one of the first and second bores can terminate prior to the outer surface, such bore(s) including an end wall that is opposed to the second tissue engaging surface. A distance between the end wall and the second tissue engaging surface can be less than a length of the respective first or second electrically insulative stop disposed in the at least one of the first and second bores that terminates prior to the outer surface measured along a length of the bore. As a result, the second electrically insulative stop protrudes from the second tissue engaging surface.

In some embodiments, at least one of the first and second electrically insulative stops can include glass. In some embodiments, including but not limited to those in which at least one of the first and second electrically insulative stops include glass, at least one of the first and second electrically insulative stops can include ceramic.

The first and second jaws of the surgical device can be bipolar, although they do not have to be configured as such.

In another exemplary embodiment, a surgical device includes a jaw assembly, at least one electrically insulative stop, an actuator operably connected to the jaw assembly to move the jaw assembly between an open configuration and a fully compressed configuration, and a driver that is configured to deliver energy to an electrode associated with the jaw assembly. The jaw assembly includes a first jaw and a second jaw that are pivotably coupled, with the first jaw having a first tissue engaging surface and the second jaw having a second tissue engaging surface, the second tissue engaging surface being opposed to the first tissue engaging surface. The first tissue engaging surface includes the aforementioned electrode to which the driver delivers energy. Energy is delivered to the electrode to seal tissue disposed between the first and second jaws when the jaw assembly is in the fully compressed configuration. The second jaw has formed in it at least one bore extending from the second tissue engaging surface and toward an outer surface of the second jaw that is opposed to the second tissue engaging surface. The at least one electrically insulative stop is disposed in the at least one bore that is formed in the second jaw. In the fully compressed configuration, at least one of the first and second jaws applies a force to the respective first or second tissue engaging surface of the other of the first and second jaws, while in the open configuration, neither of the first and second jaws applies a force to the respective first or second tissue engaging surface of the other of the first and second jaws. When the jaw assembly is in the fully compressed configuration, the at least one electrically insulative stop is engaged with the first tissue engaging surface, the second jaw is electrically isolated from the electrode of the first jaw, and a gap generally formed between the first and second jaws has a consistent size.

In some embodiments, a plurality of electrically insulative stops can be disposed in a bore of the at least one bore that is formed in the second jaw. At least one, but not all, of the plurality of electrically insulative stops can protrude from the second tissue engaging surface.

The at least one bore extending from the second tissue engaging surface and toward the outer surface can include a first bore formed in a distal portion of the second jaw and a second bore formed in a proximal portion of the second jaw. In such instances, a first electrically insulative stop of the at least one electrically insulative stops can be disposed in the first bore and a second electrically insulative stop of the at least one electrically insulative stops can be disposed in the second bore. In some instances, the at least one bore extending from the second tissue engaging surface and toward the outer surface can include a third bore formed in the proximal portion of the second jaw, with the second and third bores being disposed on opposite sides of a central longitudinal axis of the second jaw. In such instances, a third electrically insulative stop of the at least one electrically insulative stops can be disposed in the third bore. Further, the second and third stops can be aligned such that a horizontal axis extending between centers of the second and third stops is approximately perpendicular to the central longitudinal axis of the second jaw.

In some embodiments, the at least one electrically insulative stop can include a glass bead. In some embodiments, including but not limited to those in which the at least one electrically insulative stops include a glass bead, the at least one electrically insulative stop can include a ceramic bead.

The jaw assembly can be bipolar, although it does not have to be configured as such.

In one exemplary surgical method, the method includes inserting one or more electrically insulative stops into one or more bores formed in a second jaw that is pivotally coupled to a first jaw to set a desired distance for a gap formed between a first tissue engaging surface of the first jaw and a second tissue engaging surface of the second jaw, and securing a location of the one or more electrically insulative stops within respective one or more bores such that at least one of the one or more electrically insulative stops disposed in each bore of the one or more bores protrudes from the second tissue engaging surface of the second jaw. The method can further include clamping tissue between a first tissue engaging surface of a first jaw and a second tissue engaging surface of a second jaw. The first tissue engaging surface has an electrode associated with it. The clamping action results in the first jaw applying a force to the one or more electrically insulative stops such that the gap has the desired distance between the first and second tissue engaging surfaces. The method further includes delivering energy to the electrode to seal the clamped tissue, and moving the first jaw away from the second jaw to release the clamped tissue. The method further includes another clamping action, with tissue being clamped between the first tissue engaging surface and the second tissue engaging surface. The clamping action again results in the first jaw applying a force to the one or more electrically insulative stops such that the gap has the desired distance between the first tissue engaging surface and the second tissue engaging surface. A size of the gap in both clamping steps is uniform. The method further includes delivering energy to the electrode to seal the clamped tissue, and moving the first jaw away from the second jaw to release the clamped tissue.

In some embodiments, the one or more electrically insulative stops can include a first electrically insulative stop disposed in a first bore of the one or more bores that is formed in a distal portion of the second jaw and a second electrically insulative stop disposed in a second bore of the one or more bores that is formed in a proximal portion of the second jaw. As a result, when performing both clamping steps, the first jaw applies a force to each of the first and second electrically insulative stops such that a size of the gap is uniform at proximal and distal portions of the first and second jaws. A third electrically insulative stop can also be associated with the second jaw. For example, it can be disposed in a third bore of the one or more bores that is formed in the proximal portion of the second jaw, with the second and third bores and the second and third electrically insulative stops being disposed on opposite sides of a central longitudinal axis of the second jaw. The second and third electrically insulative stops can be aligned such that a horizontal axis extending between centers of the second and third electrically insulative stops is approximately perpendicular to the central longitudinal axis of the second jaw. As a result, when performing both clamping steps, the first jaw applies a force to each of the first, second, and third electrically insulative stops such that a size of the gap is uniform at proximal and distal portions of the first and second jaws.

In some embodiments, the one or more electrically insulative stops can include one or more beads made of at least one of glass and ceramic, with each of the one or more beads being disposed in the one or more bores formed in the second jaw.

BRIEF DESCRIPTION OF DRAWINGS

This disclosure will be more fully understood from the following detailed description taken in conjunction with the accompanying drawings, in which.

DETAILED DESCRIPTION

Figure 1:
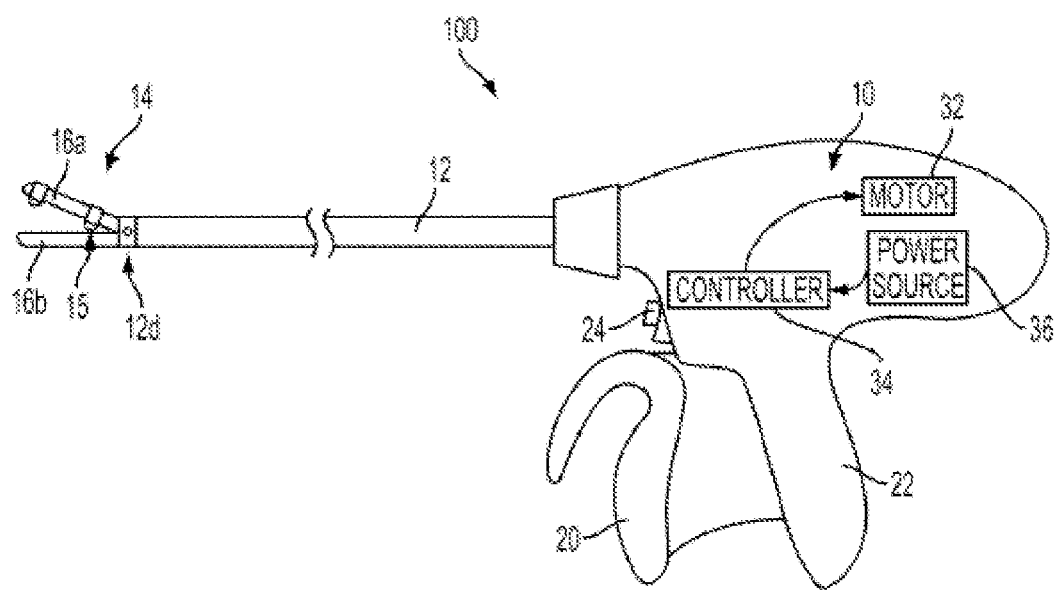
FIG. 1 is a side schematic view of one exemplary embodiment of a surgical access device having an end effector for grasping, sealing, and transecting tissue.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the various embodiments generally have similar features when those components are of a similar nature and/or serve a similar purpose. Additionally, to the extent features or sides of a structure are described herein as being a "first feature" or "first side" or "first jaw" or a "second feature" or "second jaw" or "second side," such numerical ordering is generally arbitrary, and thus such numbering can be interchangeable.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Further, a person skilled in the art will recognize that a number of different terms can be used interchangeably while still being understood by the skilled person. By way of non-limiting example, the terms "cut" and "transect" as well as "instrument" and "device" are generally used interchangeably herein. To the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape.

Surgical devices are provided herein that set a uniform gap between jaws of an end effector of the surgical devices, and further, electrically isolate one of the jaws that includes an electrode from an opposed jaw. The uniform gap can be maintained across a plurality of strokes when nothing is disposed between the jaws, or alternatively, when the thickness of an object, material, tissue, vessel, etc. disposed between the jaws is maintained across the plurality of strokes. As described herein, the uniform gap and electrical isolation is achieved by including one or more gap setters, sometimes referred to herein as electrically insulative stops, as part of at least one of the jaws of the end effector. When the device is actuated such that the first and second jaws are in a fully compressed or closed configuration, the gap setter(s) contacts the tissue engaging surface of the opposite jaw to create a buffer between the jaws. Additionally, when the gap setter(s) is non-conductive, i.e., it is an electrically insulative stop(s), the gap setter(s) electrically isolates one jaw from the other jaw.

Surgical Access Devices

FIG. 1 illustrates one embodiment of a surgical access device or instrument 100 configured to grasp and cut tissue. The surgical access device 100 can include a proximal actuator portion 10, a shaft portion 12, and a distal end effector assembly or end effector 14 configured to grasp tissue. The proximal actuator portion 10 can be any type of pistol-grip or other type of handle known in the art that is configured to carry various actuators, such as actuator levers, triggers, or sliders that can control functionality of the end effector 14. In some embodiments, the proximal actuator portion 10 can also be configured for use with a robotic surgery platform, as opposed to a user's hand. As in the illustrated embodiment, the proximal actuator portion 10 can include a closure grip 20 and a stationary grip 22. Movement of the closure grip 20 toward and away from the stationary grip 22, such as by manual movement by a hand of a user, can adjust a position of the end effector 14. The shaft portion 12 can extend distally from the proximal actuator portion 10 and can have a bore (not shown) extending therethrough. The bore can carry mechanisms for actuating the end effector 14, such as a jaw closure tube and/or a drive shaft. The instrument 100 can be configured for purely mechanical user-powered operation via the use of various linkages, gear sets, etc. Alternatively, and as shown in FIG. 1, the instrument 100 can include one or more motors 32 (e.g., an electric motor) coupled to a power source 36 (e.g., a battery) and one or more controllers 34 (e.g., a digital data processor) that can provide power for operating the device in response to sensed actuation of one or more triggers or other control mechanisms.

Figure 2:
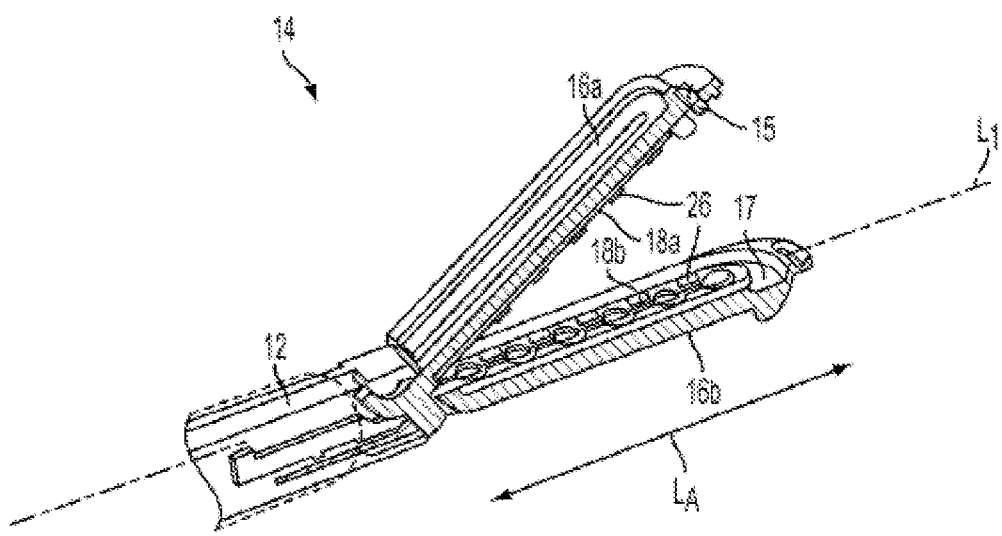
FIG. 2 is a perspective partial cross-sectional view of an end effector assembly of the surgical access device of FIG. 1.

The end effector assembly 14 can have a variety of sizes, shapes, and configurations. As shown in FIGS. 1 and 2, the end effector 14 can include a first, upper jaw 16a and a second, lower jaw 16b each disposed at a distal end 12d of the shaft portion 12, the first and second jaws 16a, 16b being collectively referred to as a jaw assembly. One or both of the upper and lower jaws 16a, 16b can be configured to close or approximate about a longitudinal axis $L_1$ of the end effector 14. Both of the jaws 16a, 16b can be moveable relative to the shaft portion 12 such that the end effector 14 can be moved between open and closed positions or configurations, or only one of the upper and lower jaws 16a, 16b can be configured to move relative to the shaft portion 12 and to the other of the jaws 16a, 16b so as to move the end effector 14 between open and closed positions. When the end effector 14 is in the open position, the jaws 16a, 16b can be positioned at a distance apart from one another with space therebetween. In use, tissue can be positioned within the space between the jaws 16a, 16b. When the end effector 14 is in the closed position, a longitudinal axis of the upper jaw 16a can be substantially parallel to a longitudinal axis of the lower jaw 16b, and the jaws 16a, 16b can be moved toward one another such that the distance therebetween is less than when the end effector 14 is in the open position.

In one configuration of a closed position, the jaws are in a fully compressed configuration. A fully compressed configuration describes an instance in which at least one of the jaws applies a force to the respective tissue engaging surface of the other jaw and a distance between the two jaws cannot be made smaller beyond some negligible amount, as would be understood by a person skilled in the art. This force can be applied through, for example, one or more gap setters 15, which, as shown, are associated with the jaw 16a. As described in greater detail below with respect to FIGS. 4-8, the gap setters 15 can both provide a uniform spacing between the jaws 16a, 16b when they are in the fully compressed configuration, and further, at least in some instances, can electrically isolate one jaw from the other.

In the illustrated embodiment, the upper jaw 16a is configured to pivot relative to the shaft portion 12 and relative to the lower jaw 16b while the lower jaw 16b remains stationary. The jaws 16a, 16b can have a substantially elongate and straight shape, but a person skilled in the art will appreciate that one or both of the jaws 16a, 16b can be curved along the longitudinal axis $L_1$ of the end effector 14. The longitudinal axis $L_1$ of the end effector 14 can be parallel to and coaxial with a longitudinal axis of the shaft portion 12 at least when the end effector 14 is in the closed configuration and, if the end effector 14 is configured to articulate relative to the shaft portion 12, when the end effector 14 is not articulated relative to the shaft portion 12.

The jaws 16a, 16b can have any suitable axial length $L_A$ for engaging tissue, where the axial length $L_A$ is measured along the longitudinal axis $L_1$ of the end effector 14, as shown in FIG. 2. The axial length $L_A$ of the jaws 16a, 16b can also be selected based on the targeted anatomical structure for transection and/or sealing. In one embodiment, the jaws 16a, 16b can have a substantially equal axial length $L_A$, though use of different length jaws is possible in other embodiments.

The jaws 16a, 16b can have any number and any combination of features configured to facilitate grasping tissue between the facing surfaces 18a, 18b of the jaws 16a, 16b. The first and second engagement surfaces 18a, 18b can each be configured to directly contact tissue. Either one or both of the engagement surfaces 18a, 18b can include one or more surface features formed thereon that can help secure the tissue thereon. The one or more surface features can facilitate grasping of tissue, can be configured to increase friction between the tissue and the engagement surfaces 18a, 18b of the jaws 16a, 16b without tearing or otherwise damaging the tissue in contact with such surface features, and/or can facilitate forming substantially smooth, uniform layers of tissue. Examples of the surface features can include teeth, ridges, and depressions. In the illustrated embodiment of FIG. 2, the jaws 16a, 16b each include a plurality of teeth 26 positioned along an axial length of both of the engagement surfaces 18a, 18b.

Further, at least one of the jaws, as shown the lower jaw 16b, can include one or more electrodes 17 disposed on a tissue engagement surface 18b of the jaw 16b. While a person skilled in the art will recognize that the number, location, and configuration of the electrode(s) 17 associated with one or both jaws 16a, 16b can have a variety of configurations, generally the electrode 17 is configured to supply energy to tissue disposed between the jaws 16a and 16b to coagulate or seal the tissue. The electrode 17 can be coupled to the engagement surface 18b using any manner known to those skilled in the art, including, by way of non-limiting example, using an adhesive. The electrode 17 can cover any portion, or even an entire portion, of the tissue engagement surface 18b. In the illustrated embodiment, the electrode 17 covers a substantial majority of a substantially flat portion of the tissue engagement surface 18b, leaving the teeth 26 exposed to engage with tissue, and thus tissue disposed at the electrode 17 generally engages the electrode 17 rather than a substantially flat portion of the tissue engagement surface 18b. While a person skilled in the art will generally understand what constitutes "cover[ing] a substantial majority of a substantially flat portion of [a] tissue engagement surface" in view of the present disclosures, generally the electrode covers at least 80%, if not more, of the tissue engagement surface. In some exemplary embodiments, the jaw assembly is bipolar, although it could be monopolar or have other types of configurations known to those skilled in the art.

In some exemplary embodiments, the electrode can be made from a positive temperature coefficient (PTC) polymer or matrix that provides homogeneous and precisely regulated energy delivery with low thermal spread. The PTC conductive-resistive matrix can be a variably resistive body that comprises a polypropylene or a medical grade silicone polymer that is doped with conductive particles (e.g., carbon). Polymer PTC materials are known in the field of over current protection devices that will "trip" and become resistant when a selected trip current is exceeded. Although in the illustrated embodiments the electrode 17 is associated with only the lower jaw 16b, in other embodiments, one or more electrodes can be disposed on only the upper jaw 16a or on both the upper and lower jaws 16a and 16b. Likewise, any number of electrodes can be used on either jaw 16a and 16b.

The jaws 16a, 16b can include an insulator material associated with the jaws. For example, the insulator material can be coated on the jaws 16a, 16b to help insulate the portions of the jaws through which energy passed to the electrode 17 does not need to be passed for purposes of sealing tissue. A person skilled in the art will recognize ways by which the insulator material can be coated on or otherwise associated with the jaws 16a, 16b.

One or both of the first and second jaws 16a, 16b can include one or more features configured to interact with a cutting element for cutting tissue or a compression member 28 (see FIG. 3) for applying compressive forces on the jaws 16a, 16b and/or tissue, as well as to optionally cut tissue. For example, the first and second jaws 16a, 16b can includes slots configured to receive portions of the cutting element, as shown in FIG. 2, so that the cutting element 28' can travel through the jaws 16a, 16b to cut tissue disposed between the jaws. In alternative embodiments, the slots can include additional recessed portions that are complementary to flanges 30a, 30b disposed on the compression member 28 and act as a track to direct movement of the compression member. A person skilled in the art will recognize various configurations of a cutting element like the one illustrated in FIG. 2, including various sizes, shapes, and configurations, and thus additional disclosure related to the same is not required.

Figure 3:
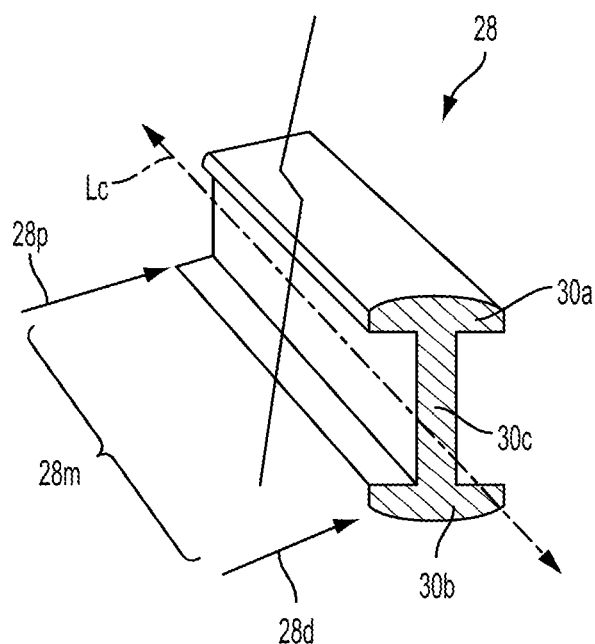
FIG. 3 is a detail perspective view of a compression member for use in conjunction with a surgical access device, such as the device of FIG. 1.

The compression member 28 can also have various sizes, shapes, and configurations. The compression member can have an elongate shape and can be moveable proximally and distally along the longitudinal axis $L_1$ of the end effector 14. As shown in FIG. 3, the compression member 28 can have a proximal end 28p, a distal end 28d, and a medial portion 28m extending therebetween. The proximal end 28p and the medial portion 28m of the compression member 28 can be sized and shaped to reciprocate within the shaft portion 12 of the instrument 100. The distal end 28d of the compression member 28 can be sized and shaped to interact with the jaws 16a, 16b of the end effector 14. A longitudinal axis $L_C$ of the compression member 28 can be parallel to and coaxial with the longitudinal axis $L_1$ of the end effector 14, though other configurations are possible. The compression member 28 can be actuated from the proximal handle portion 10 of the instrument 100 by a firing actuator or trigger 24 that is operatively coupled to the proximal end 28p of the compression member 28, such as via a depressible button. Other examples of the firing actuator that can actuate the compression member include a lever, a knob, a switch, and a trigger. In general, the firing trigger 24 can be configured to be manually manipulated by a user to cause actuation of one or more other instrument elements, such as the compression member 28.

The compression member 28 can include a connecting portion 30c and upper and lower flanges 30a, 30b, thus providing an "I" cross-sectional shape for the compression member 28. As in the illustrated embodiment, the upper and lower flanges 30a, 30b can be positioned substantially perpendicular to the connecting portion 30c to form the "I" cross-sectional shape. The upper and lower flanges 30a, 30b can be sized and shaped to allow the upper and lower flanges 30a, 30b to slide in the above-mentioned recessed slots in the upper and lower jaw 16a, 16b, respectively. This sliding contact of lateral edges of the flanges 30a, 30b and sides of each of the recessed slots can prevent lateral flexing of the jaws 16a, 16b. The compression member 28 can have various other configurations. For example, the upper flange 30a can have a width that is greater than a width of the lower flange 30b, the widths being measured in a direction perpendicular to the longitudinal axis $L_1$ of the end effector 14.

The compression member 28 can form a distal tip of a drive shaft that moves through the end effector 14 such that only a distal portion of the drive shaft includes the compression member 28. A longitudinal length of the compression member 28 can be less than a longitudinal length of the end effector 14 such that the distal tip that includes the compression member 28 can move through the end effector 14 without the compression member 28 extending along the entire longitudinal length of the end effector 14. Alternatively, the compression member 28 can extend along an entire longitudinal length of the drive shaft. The compression member 28 can thus extend along the end effector's entire longitudinal length when the compression member 28 is in its distal-most position relative to the end effector 14.

The instrument 100 can include a cutting element (not shown) configured to cut tissue captured between the jaws 16a, 16b. The cutting element can have various sizes, shapes, and configurations. Examples of the cutting element include a knife blade and a sharp edge. The cutting element can be sized and shaped to cut various thicknesses and types of tissue positioned between the jaws 16a, 16b of the end effector 14. In an exemplary embodiment, the cutting element can be positioned at the distal end 28d of the compression member 28, such as by being formed on the connecting portion 30c of the compression member 28 as an integral part thereof, e.g., as a sharpened edge thereof, or as a member attached thereto, e.g., a blade mounted thereon. The cutting element can have a sharp or serrated edge configured to transect tissue. In an exemplary embodiment, the cutting element can be recessed relative to distal ends of upper and lower flanges 30a, 30b of the compression member 28, which can allow compression to occur prior to the cutting element cutting tissue as the compression member 28 traverses through the jaws 16a, 16b. In such an embodiment, the compression member 28 including a sharpened edge cutting element can form a cutting mechanism of the instrument 100 that can transect tissue disposed between the jaws 16a, 16b. In another embodiment, the cutting element can be configured such that it is not attached to the compression member 28, such that the cutting element can be configured to advance and retract relative to the jaws 16a, 16b so as to cut tissue sandwiched therebetween without applying compression to the tissue. In such an embodiment, the instrument 100 can include a separate compression member so that tissue engaged by the jaws 16a, 16b can still be compressed.

The surgical instrument 100 can include a second, closure actuator or trigger configured to open and close the jaws 16a, 16b of the end effector 14. Manipulation of the closure actuator, e.g., manual manipulation by a user, can cause the end effector 14 to move between the open and closed positions. In other words, manipulation of the closure actuator can cause one or both of the jaws 16a, 16b to pivot or otherwise move, as discussed above, so as to allow the jaws 16a, 16b to engage tissue, move anatomical structures, and/or perform other surgical functions. The closure actuator can have various sizes, shapes, and configurations. As in the illustrated embodiment, the closure actuator can include the closure grip 20 and the stationary grip 22. The closure grip 20 can be moveable toward and away from the stationary grip 22, such as via pivoting. The closure grip 20 can have a first position in which the closure grip 20 is angularly offset from the stationary grip 22 and in which the jaws 16a, 16b are open. The closure grip 20 can have a second position that is different from the first position and in which the closure grip 20 is positioned adjacent to, or substantially in contact with, the stationary grip 22 and in which the jaws 16a, 16b can engage tissue and apply a force to tissue disposed therebetween. The closure grip 20 can be biased to the first position with the jaws 16a, 16b being open, as shown in FIG. 1.

The closure grip 20 can be configured to move the jaws 16a, 16b between the open and closed positions using manual or powered components. In a manually actuated embodiment, the closure grip 20 can be coupled to a gear that interacts with a rack extending in the handle portion 10, and manual movement of the closure grip 20 toward the stationary grip 22 can move the rack distally toward the end effector 14, causing a force to be exerted onto the jaws 16a, 16b to close the jaws 16a, 16b. In addition to a gear and rack, however, a number of other mechanical linkages are also possible.

In a powered embodiment, as shown in the illustrated embodiment of FIG. 1, the instrument 100 can include a motor 32, a controller 34, and a power source 36. The motor 32, the controller 34, and the power source 36 can be disposed in the proximal actuator portion 10. The motor 32 can include any type of motor (e.g., a rotary motor, etc.) configured for use with a surgical instrument, the controller 34 can include a variety of devices configured to process signals (e.g., a microprocessor, a central processing unit (CPU), a memory controller, etc.), and the power source 36 can include a variety of devices configured to supply power to at least the controller 34 (e.g., a battery, etc.). In some embodiments, the power source can be off-board instead of on-board the instrument 100, such as by the instrument 100 being attachable via wired connection to an electrical outlet or other power source. In some embodiments, the motor can be off-board instead of on-board the instrument 100, such as by being attachable via a wired connection to the motor. A manual movement of the closure grip 20 can be configured to cause the controller 34 to transmit a control signal to the motor 32, which can cause the jaws 16a, 16b to close via movement of the compression member 28. The closure grip 20 can interact with one or more locking features (not shown) configured to lock the closure grip 20 relative to the stationary grip 22. For example, the one or more locking features can automatically engage when the closure grip 20 substantially contacts the stationary grip 22.

The firing and closure actuators or triggers can cooperate to allow selective firing and closing of the instrument 100. The firing trigger 24 can be configured to be actuated to advance the cutting element through the end effector 14, apply energy to tissue, or both. Depressing or pivoting the firing trigger 24 can activate various elements in the instrument, and thereby cause one or more actions such as the compression member 28 and/or the cutting element advancing distally relative to the jaws 16a, 16b, and/or the compression member 28 and/or the cutting element retracting proximally relative to the jaws 16a, 16b, and/or energy being delivered to the jaws 16a, 16b. In a motor-powered embodiment, the firing trigger 24 can be in electrical communication with the motor 32 and the motor 32 can be operatively coupled to the compression member 28 using, e.g., a gear and rack. In such an embodiment, activation of the motor 32 can cause advancement and/or retraction of the compression member 28.

In a motor-powered embodiment, the instrument 100 can include at least one sensor (not shown) and the motor 32 can be configured to provide an output that is based at least in part on an output from the sensor. The controller 34 can be configured to determine an amount of power to be provided by the motor 32. The controller 34 can be configured to receive an output signal from the sensor, and based on the output signal from the sensor, cause the motor 32 to provide an output that supplies power to the cutting element. As discussed herein, the motor and the controller may not be disposed within the surgical instrument, e.g., may not be disposed within a handheld proximal actuator portion thereof. Instead, the motor and/or the controller can be located in a separate interface or within a generator to which the surgical instrument can be configured to operatively connect, as discussed further below. In other embodiments, however, the instrument can be manually powered by a user's movement of the various actuators or triggers using mechanical linkages to translate trigger movement into distal end effector operation.

The surgical access device 100 can also be configured to provide energy, e.g., radio frequency (RF) energy or other therapeutic treatment energy, to tissue clamped between the jaws 16a, 16b. The firing trigger 24 can be configured to cause application of the energy in some embodiments. The energy can be applied in a variety of manners. Examples of applying energy are described further in U.S. Pat. Pub. No. 2012/0078139, entitled "Surgical Generator For Ultrasonic And Electrosurgical Devices," filed Oct. 3, 2011, U.S. Pat. No. 9,161,803, entitled "Motor Driven Electrosurgical Device With Mechanical And Electrical Feedback," filed Jun. 2, 2011, and issued, Oct. 20, 2015, and U.S. Pat. Pub. No. 2015/0209573, entitled "Surgical Devices Having Controlled Tissue Cutting And Sealing," filed on Jan. 28, 2014, the entire contents of each which are hereby incorporated by reference in their entireties.

Jaw Assemblies and Gap Setters

Figure 4A:
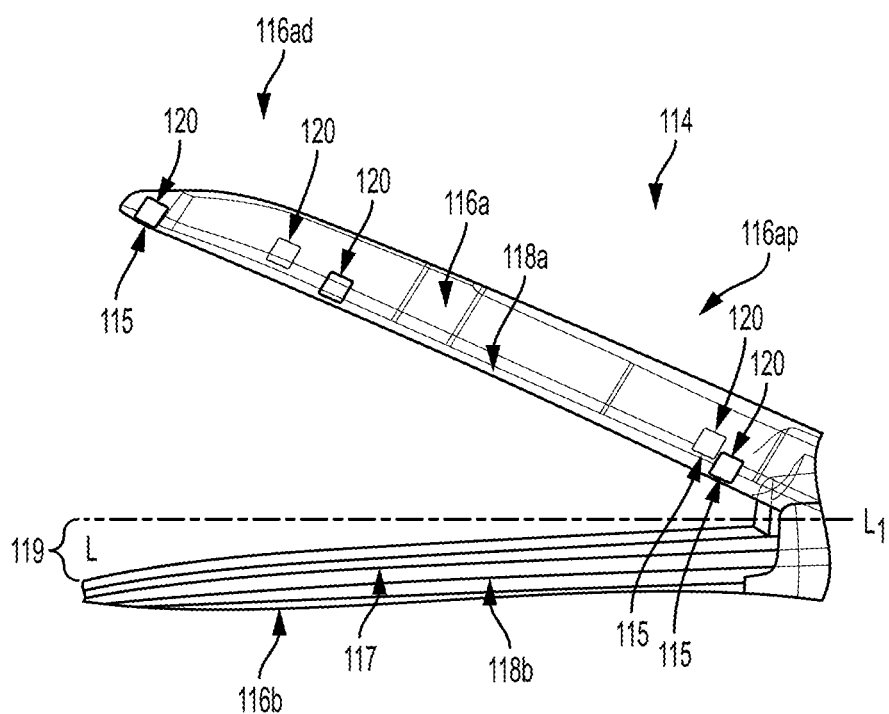
FIG. 4A is a partially transparent side view of one exemplary embodiment of an end effector assembly that can be part of a surgical access device like the surgical access device of FIG. 1.
Figure 4B:
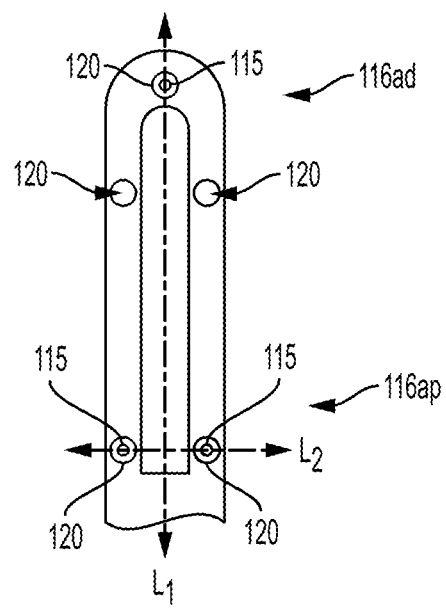
FIG. 4B is a top schematic view of the end effector assembly of FIG. 4A illustrating a location of gap setters with respect to other portions of the end effector assembly.

FIGS. 4A and 4B illustrate another exemplary embodiment of an end effector or end effector assembly 114 in accordance with the teachings of the present disclosure. The end effector 114 can be used with the surgical access device 100 in place of the end effector assembly 14 illustrated in FIG. 1, or with other surgical access devices that are derivable from the present disclosure or otherwise known to those skilled in the art. As shown, the end effector 114 is a jaw assembly that includes a first, upper jaw 116a and a second, lower jaw 116b that are pivotally coupled to each other with one jaw, as shown the second jaw 116b, having an electrode 117 associated therewith, and the other jaw, as shown the first jaw 116a, having a plurality of gap setters 115 associated therewith. More particularly, the gap setters 115 are disposed in the first jaw 116a and protrude from a tissue engaging surface 118a of the first jaw 116a, towards the second jaw 116b. The gap setters 115 prevent the tissue engagement surface 118a of the upper jaw 116a from coming directly into contact with the electrode 117 associated with a tissue engagement surface 118b of the lower jaw 116b. This, in turn, provides for a gap or space 119 to be formed between the two jaws 116a, 116b when the jaws are in a fully compressed configuration with no tissue being disposed between the jaws 116a, 116b.

The gap setters 115 can have a variety of configurations, and in the illustrated embodiment the gap setters 115 have a cylindrical shape, with the gap setters 115 sometimes being referred to as beads, balls, and/or posts. A diameter of the gap setters 115 can be approximately in the range of about 0.1 millimeters to about 10 millimeters. Further, the amount a gap setter can protrude from the tissue-engaging surface with which it is associated can be approximately in the range of about 0.1 millimeters to about 5 millimeters. The size and shape of the gap setters 115, and the amount it protrudes from the tissue-engaging surface 118a with which it is associated can depend on a variety of factors, including but not limited to the size and shape of the other components of the instrument with which they are used, the number of gap setters being used, and a desired gap to be formed between the jaws by contacting one of the jaws with the gap setters associated with the other jaws, among others.

Further, a number of different materials can be used to form the gap setters 115. While almost any material can be used, in embodiments in which the gap setters 115 are designed to be electrically isolating or non-conductive such that electrical current does not pass from one jaw to the other via the gap setters 115, the material(s) used to form the gap setters 115 includes insulating or non-conductive properties. In such instances, the gap setters 115 can be referred to as electrically insulative stops. Some non-limiting examples of non-conductive materials that can be used to form electrically insulative stops 115 include but are not limited to glass, a Pyrex®-like glass or similar material, ceramics, non-conductive ball bearings, polymer, plastic, and ceramic posts. In embodiments in which there are multiple gap setters, each gap setter can have the same shape and/or be made of the same substance, or alternatively, the various gap setters can be sized and made from one or more different materials as desired.

Due to the gap setters 115 providing a uniform gap 119 between the jaws when they are in the fully compressed configuration, overcompression is avoided. This is because an optimal amount of force can be applied consistently to the tissue during every stroke. In this configuration, the gap setters 115 regulate the desired contact area of the jaws 116a, 116b with the grasped tissue, thereby eliminating undesired burning or charring of the tissue. Further, in embodiments in which the gap setters 115 are electrically insulative stops, the electrical isolation prevents the electrode from contacting the tissue engaging surface of the opposite jaw, thereby helping to eliminate erosion of insulator material that is associated with the jaws 116a, 116b. Notably, although the gap is described as being uniform, that does not mean that the space formed between the opposed surfaces of the jaws 116a, 116b is consistent across a length or width of the jaw assembly. Rather, it means that the space at a given location is uniform after each stroke provided nothing is disposed between the jaws 116a, 116b, or if something is disposed between the jaws 116a, 116b, its thickness is maintained between the strokes. A stroke is considered to be movement of the jaw assembly from an open configuration to a closed configuration, and then a return of the jaw assembly to the open configuration by pivoting the first jaw away from the second jaw to release the clamped tissue. The closed configuration can be a fully compressed configuration that is used to transect or seal tissue that is disposed between the jaws.

Figure 5A:
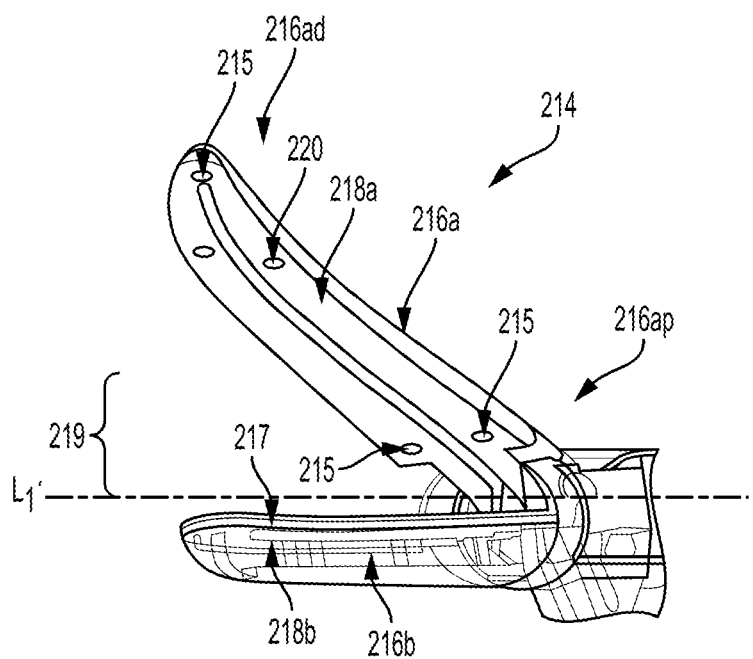
FIG. 5A is a partially transparent perspective side view of another exemplary embodiment of an end effector assembly that can be part of a surgical access device like the surgical access device of FIG. 1.
Figure 5B:
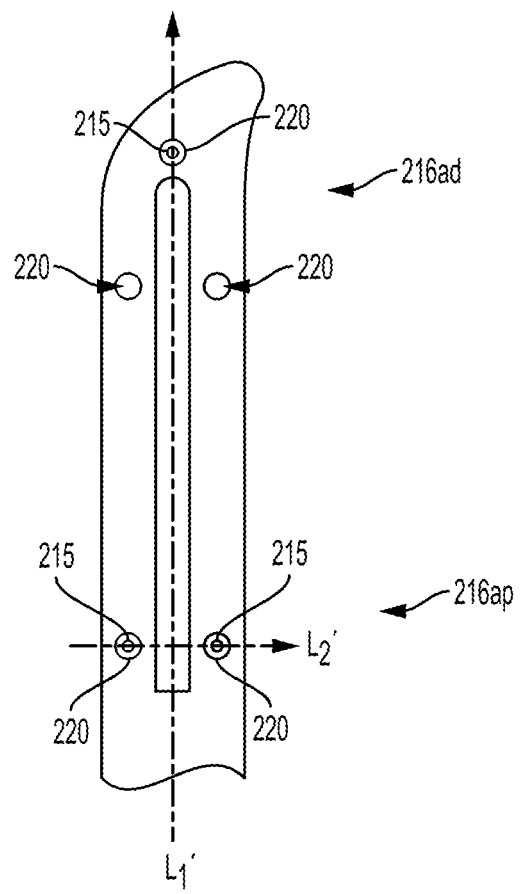
FIG. 5B is a top schematic view of the end effector assembly of FIG. 5A illustrating a location of gap setters with respect to other portions of the end effector assembly.

FIGS. 5A and 5B provide for an alternative exemplary embodiment of an end effector or end effector assembly 214 in accordance with the teachings of the present disclosure. The end effector 214 can be used with the surgical access device 100 in place of the end effector assembly 14 illustrated in FIG. 1, or with other surgical access devices that are derivable from the present disclosures or otherwise known to those skilled in the art. The end effector 214 is similar to the end effector 114 except that a first, upper jaw 216a has a curved configuration in which a length of the upper jaw 216a is curved along a longitudinal axis $L_1'$ of the end effector 214. As shown, a longitudinal axis $L_1'$ of the end effector 214 can be parallel to and coaxial with a longitudinal axis of a shaft portion of a surgical access device, e.g., the shaft portion 12 of the instrument 100, at least when the end effector 214 is in the closed configuration and, if the end effector 214 is configured to articulate relative to the shaft portion, when the end effector 214 is not articulated relative to the shaft portion. Other components of the end effector 214 that have similar features as the end effector 114 include but are not limited to: an electrode 217 associated with a second, lower jaw 216b that is pivotally coupled with the upper jaw 216a; the electrode 217 being disposed on a tissue engagement surface 218b of the second jaw 216b; gap setters 215 disposed in the first jaw 216a and protruding from a tissue engagement surface 218a of the first jaw, towards the second jaw 216b; and the gap setters 215 providing for a gap or space 219 that is formed between the jaws 216a, 216b.

The gap setters 115, 215 can be positioned at any location with respect to the tissue engaging surface of the jaw within which they are disposed. In the illustrated embodiments of FIGS. 4A-4B and 5A-5B, the gap setters 115, 215 are associated with upper jaw 116a, 216a. More particularly, each of the end effectors 114, 214 includes three gap setters 115, 215 associated with the respective upper jaw 116a, 216a. As shown, a single gap setter 115, 215 is disposed at a distal end 116ad, 216ad of the respective upper jaw 116a, 216a, and two gap setters 115, 215 are disposed at a proximal end 116ap, 216ap of the respective upper jaw 116a, 216a, on opposed sides of the central longitudinal axis $L_1$, $L_1'$. In particular, as shown in FIGS. 4B and 5B, the location of the gap setters 115, 215 at the proximal ends 116ap, 216ap can be aligned such that a horizontal axis $L_2$, $L_2'$ that extends between their respective centers is approximately perpendicular to the central longitudinal axis $L_1$, $L_1'$ of the end effector 114, 214. The alignment of gap setters 115, 215 in the illustrated embodiment can maintain the gap between the jaws at that location in the event that one of the gap setters 115, 215 dislodges. In other embodiments, gap setters disposed on opposed side of the central longitudinal axis $L_1$, $L_1'$ may not be aligned such that a horizontal axis extends between their respective centers with the horizontal axis being approximately perpendicular to the central longitudinal axis $L_1$, $L_1'$. Further, a larger number of gap setters 115, 215 can provide for a gap that is more uniform and more consistent in size between the jaws in the fully compressed configuration.

The number of gap setters 115, 215 that are associated with the upper jaw 116a, 216a can vary. For example, in one embodiment, the upper jaw 116a, 216a can be configured to have a first gap setter 115, 215 located at the distal end 116ad, 216ad of the upper jaw 116a, 216a and a second gap setter 115, 215 located at a proximal end 116ap, 216ap of the upper jaw 116a, 216a. The distance between the two gap setters 115, 215 can vary as can be appreciated by one skilled in the art such that the upper jaw 116a, 216a is sufficiently electrically isolated from the electrode 117, 217 of the lower jaw 116, 216 in the fully compressed configuration.

The gap setters 115, 215 can be associated with the jaws 116a, 216a using any number of techniques provided for herein or otherwise known to those skilled in the art. In the illustrated embodiment, they are disposed in bores or holes 120, 220 formed in the first jaw 116a, 216a using techniques described below. The gap setters 115, 215 can likewise be maintained in the bores 120, 220 using techniques described elsewhere in the present disclosure or using techniques known to those skilled in the art for maintaining the location of an object within at least a portion of a bore such that a portion of the object also protrudes from the bore. In the illustrated embodiments, there are five bores 120, 220, with three of the five bores including gap setters 115, 215. More particularly, two intermediate bores 120, 220 disposed between the bores 120, 220 located at the proximal and distal ends 116ap, 216ap and 116ad, 216ad do not include gap setters. In other embodiments, these intermediate bores 120, 220 can also include gap setters. A person skilled in the art will recognize that any number of bores and gap setters can be used, at any location along a length of the end effector assembly 114, 214, without departing from the spirit of the present disclosure. Thus, the configurations provided for herein are not limiting. Further, some bores may not include gap setters, while in other instances, all bores may include gap setters. It will be appreciated that while the terms bore and hole are used herein to describe elements like the bores or holes 120, 220, channels, through-holes, blind-holes, mortises, and other formations akin to bores or holes can be used with respect to certain embodiments, as described further below.

Figure 6A:
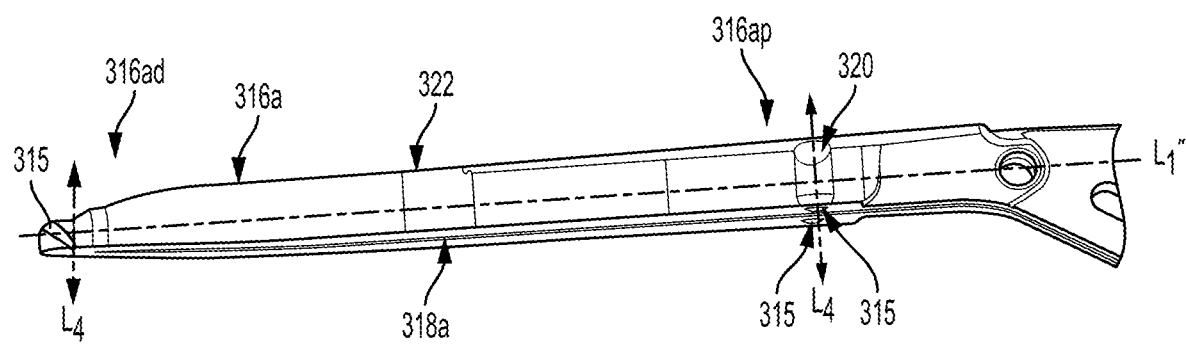
FIG. 6A is a detailed perspective side view of a top jaw of the end effector assembly of FIG. 4A.
Figure 6B:
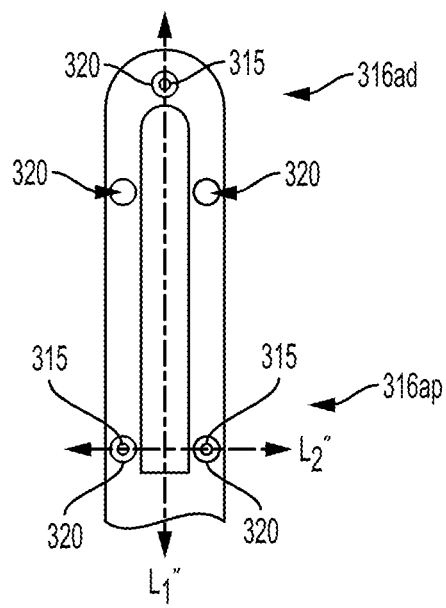
FIG. 6B is a top schematic view of the end effector assembly of FIG. 6A illustrating a location of gap setters with respect to other portions of the end effector assembly
Figure 7:
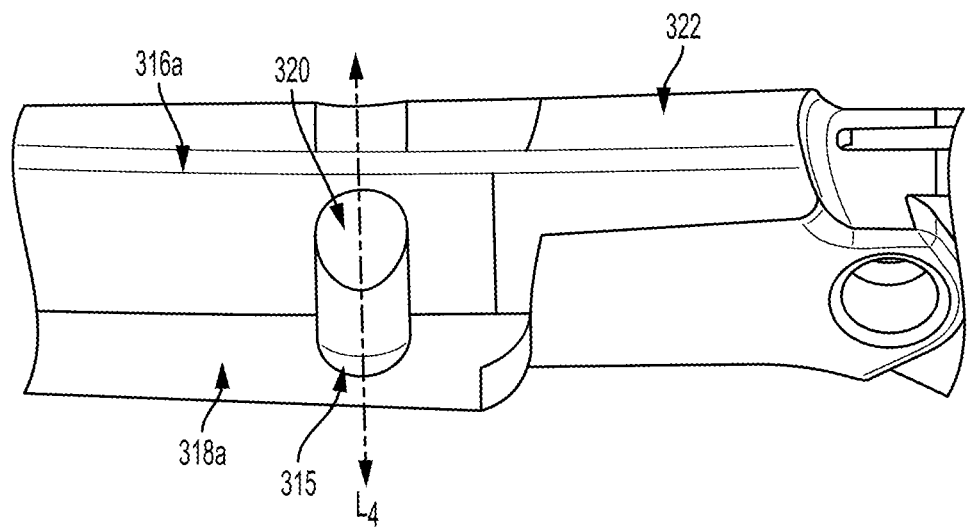
FIG. 7 is a detailed perspective top view of the top jaw of FIG. 6A.
Figure 8:
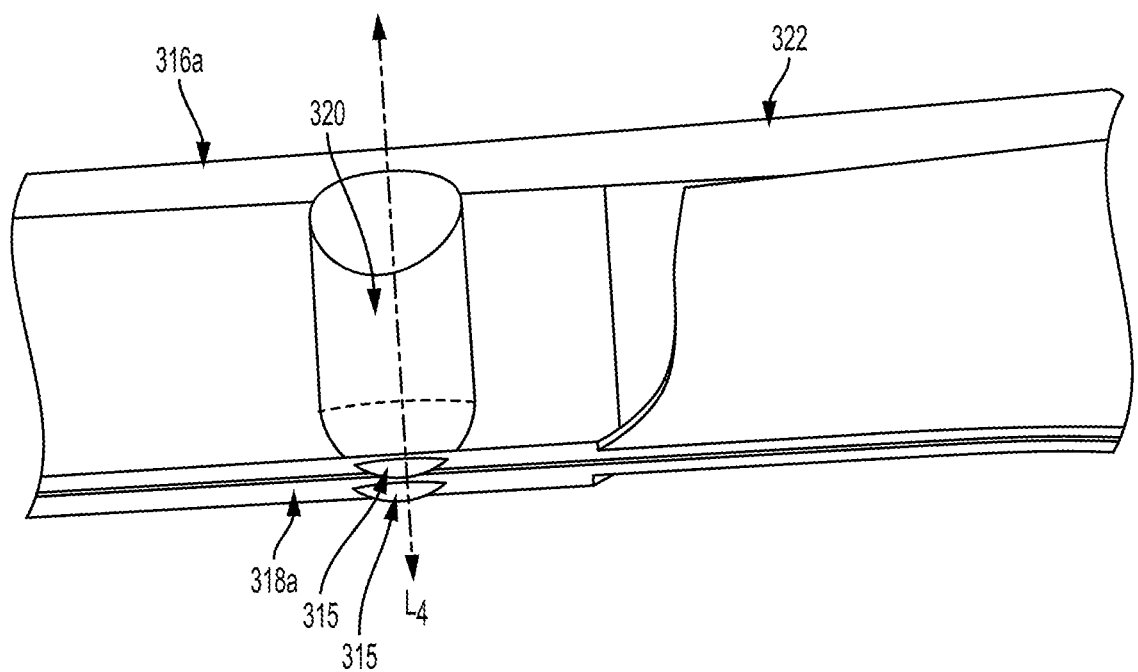
FIG. 8 is a detailed perspective side view of the top jaw of FIG. 6A.

Another embodiment that includes an upper jaw 316a having three gap setters 315 disposed therein is provided for in FIGS. 6A and 6B. The gap setters 315 can be spaced across the length of the upper jaw 316a or multiple gap setters 315 can be associated with either distal or proximal ends 316ad, 316ap of the upper jaw 316a. In the illustrated embodiment, two gap setters 315 are associated with the proximal end 316ap and a single gap setter 315 is associated with the distal end 316ad. The gap setter 315 that is located at the distal end 316ad can be centrally disposed on the upper jaw 316a such that the center of the gap setter 315 lies along the longitudinal axis $L_1''$ of the upper jaw 316a, though other configurations of the gap setter 315 at the distal end are possible.

The two gap setters 315 located in the proximal end of the upper jaw 316a of the illustrated embodiment are located on opposite sides of a central longitudinal axis $L_1''$ of the upper jaw 316a. Moreover, as shown in FIG. 6B, the gap setters 315 at the proximal end 316ap can be aligned such that a horizontal axis $L_2''$ that extends between the centers of the two gap setters 315 is approximately perpendicular to the longitudinal axis $L_1''$ of the upper jaw 316a.

Many other configurations of the gap setters 315 are possible without departing from the spirit of the present disclosure. Gap setters can be provided in any pattern that may be desirable to the user based on a variety of factors, including, but not limited to, the tissue with which the device is being used, the other components of the device, and the desired configuration of the user. In another embodiment, the horizontal axis $L_2''$ between the centers of two gap disposed on opposed side of the longitudinal axis $L_1''$ is not approximately perpendicular to the central longitudinal axis $L_1''$. In yet another embodiment, all the gap setters 315 can be associated with the proximal and/or distal end of the upper jaw 316a while lying on the same side of the longitudinal axis $L_1''$. By way of further non-limiting example, the upper jaw 316a can have a single gap setter 315 associated with either a distal or proximal end of the upper jaw 316a.

One having ordinary skill in the art can appreciate that in alternate embodiments of the device, the gap setters can be disposed within the lower jaw or in both the upper and lower jaws. Each gap setter is generally located on the periphery of the tissue engaging surface so as not to interfere with the tracks through which the cutting member travels. This orientation allows the gap setter to contact the tissue engaging surface on the opposite jaw, thereby creating a buffer between the upper and lower jaws. When a tissue to be transected or sealed lies between the jaws, the gap setter can contact the tissue in the closed configuration while still maintaining the buffer between the jaws. The location of the gap setters along the upper jaw allows teeth, or similar features that are associated with the jaws to help grasp tissue therebetween. When the electrode is actuated to seal the tissue, the presence of the gap setters ensures that the opposite jaw is electrically isolated from the electrode. The gap setters can also help to grasp and/or hold tissue between the jaws in the fully closed configuration.

Many different techniques, either known to those skilled in the art or provided for in the present disclosure, can be used to associate gap setters with jaws. For example, the upper jaw can have bores formed therein that are configured to receive gap setters. These configurations can take a variety of forms, some of which are described below and others which can be readily derived in view of the present disclosures. Some non-limiting examples of bores used in conjunction with the present disclosures are provided for in FIGS. 1, 2, 3A, 3B, 5A, 5B, 6A, 6B, 7, and 8. Further, bores can be used in conjunction with the surgical access devices 100, 200 illustrated in FIGS. 1-5, or with other surgical access devices that are derivable from the present disclosures or otherwise known to those skilled in the art.

As illustrated in FIGS. 6A-8, in one embodiment of bores, the bores 320 have a generally cylindrical shape that is configured to receive a gap setter 315 within it. As shown in FIG. 6A, each bore 320 has a central axis L4 that extends substantially perpendicular to the central axis $L_1"$ that extends through the thickness of the jaw 316a. By way of further non-limiting example, the bore 320 can form a mortis that has any shape, e.g., elliptical, round, rectangular, and so forth, capable of receiving at least a portion of the gap setter 315. The shape of the mortis can also depend, at least in part, on the shape of the gap setter.

There are various ways for the bore 320 to be oriented within the upper jaw 316a. As shown in the illustrated embodiment of FIGS. 6A-8, the bore 320 can form a through-hole or through-bore that extends from the outer surface 322 of the upper jaw 316a to the tissue engaging surface 318a of the upper jaw 316a. Formation of the through-hole can be done using techniques known by those skilled in the art for forming through-holes or similar shapes into a portion of a jaw, housing, or the like, including but not limited to by drilling through the surface of the upper jaw 316a. In other exemplary embodiments, the bore may not extend through the upper jaw 316a. For example, the bore can form a blind-hole that starts from the tissue engaging surface 318a of the upper jaw 316a and extend towards the outer surface 322 of the upper jaw 316a before terminating prior to the outer surface 322. Thus, the length of the blind-hole is less than a thickness of the upper jaw 316, where the thickness of the upper jaw 316 is defined by the distance between the tissue engaging surface 318a and the outer surface 322 and the length of the blind-hole extends in the same direction between its terminal ends. In such a configuration, a length of the blind-hole can be selected so that it is less than a diameter of the gap setter 315. As a result, at least a portion of the gap setter 315, when disposed in the blind-hole, will necessarily protrude beyond the tissue engaging surface 318a, towards a lower jaw (not shown).

While the length of the bore 320 can be less than or equal to the distance between the outer surface 322 of the upper jaw 316a and the tissue engaging surface 318a of the upper jaw 316a (i.e., the thickness of the upper jaw), in the illustrated embodiment of FIGS. 6A and 6B, the bore length is equal to the thickness of the upper jaw. Nevertheless, as shown, a portion of the gap setter 315 that is disposed in the bore 320 still extends past the tissue engaging surface 318 of the upper jaw 316a. As will be apparent to a person skilled in the art in view of the present disclosure, such a configuration can be achieved in a number of ways. In the present embodiment, a diameter of the bore 320 proximate to the tissue engaging surface 318a can be less than the diameter of the bore 320 located proximate to the outer surface 322, and the diameter of the gap setter 315 to be disposed within the bore 320 can be greater than the diameter of the bore 320 proximate to the tissue engaging surface 318 of the upper jaw 316a and less than the diameter of the bore 320 proximate to the outer surface of the upper jaw 316a. As a result, the gap setter 315 can be passed into the bore 320 across the outer surface 322 before engaging walls of the bore 320 that form the diameter that is smaller than the diameter of the gap setter, causing a portion of the gap setter 315 to extend past the tissue engaging surface 318a of the upper jaw 316a and create a uniform gap between the jaws 316a, 316b. The position of the gap setter 315 with respect to the bore 320, and thus the jaw 316a, 316b can be maintained using any number of techniques, including but not limited disposing any sort of filler and/or adhesive into the bore to hold the gap setter 315 substantially in place. Other techniques for putting pressure onto the gap setter 315 in a direction towards the tissue engaging surface 318a to hold the gap setter in place are also contemplated, including but not limited to putting multiple gap setters into the bore 320 and placing a cap (not shown) proximate to the outside surface 322 to hold the gap setters in place. The use of multiple gap setters can also be considered a form of filler, with the gap setters that do not protrude from the tissue engaging surface 318a forming at least a portion of filler. This variability allows a user to select a desired gap distance to be formed between the two jaws 316a, 316b, by selecting how far the gap setter 315 protrudes from the tissue engaging surface 318a. The gap distance can be set to be substantially uniform across an entire length of the jaws 316a, 316b, or it can be variable at different portions along the entire length of the jaws 316a, 316b, depending on a variety of factors, including but not limited to the user's preferences, the type, size, and shape of tissue or other objects being engaged, and the type of procedure being performed.

In an embodiment in which the bore 320 has one terminal end at the tissue engaging surface 318a and extends toward the outer surface 322 before terminating prior to the outer surface 322, the length of the bore 320 itself can define how far through the gap setter 315 can pass into the bore when being passed across the tissue-engaging surface 318a and toward the outside surface 322. Thus, as explained above, when the bore length is less than a diameter of the gap setter, the gap setter protrudes from the tissue-engaging surface 318a. Alternatively, the bore 320 can have a variable diameter across its length, with the length even extending through the thickness of the upper jaw 316a. The variable diameter can be figured such that it is capable of preventing the gap setter 315 from passing too far into the jaw 316a such that no portion of the gap setter protrudes beyond the tissue-engaging surface 318a. For example, at some point along the length of the bore 320, the bore can have a diameter that is less than a diameter of the gap setter 315. This can prevent the gap setter from passing too far toward the outside surface 322, allowing the gap setter to protrude beyond the tissue-engaging surface when it is situated within a portion of the bore 320. Any number of techniques can likewise be used to maintain the location of the gap setter 315 with respect to the bore 320, including using one or more adhesives or the like to hold the gap setter 315 substantially in place and/or coining the edges of the bore 320. In some embodiments, the gap setter can be held in place via interference fit, i.e., a press fit with a portion of the bore 320.

A person skilled in the art will understand the various sizes (lengths, diameters, depths, etc.) and configurations of the bores and gap setters that can be used to design the jaw 316a to achieve the desired uniform gap, i.e., configuring the jaw such that the gap setter protrudes out of the tissue-engaging surface, toward the other jaw, the desired amount. Such configurations are within the spirit of the present disclosure. By way of non-limiting example, in some embodiments the gap setters can be ceramic posts, the bores can be drilled to provide diameters similar in size to the diameters of the ceramic posts, and the posts can be glued into the bores. The lengths of the posts and bores, in addition to a location at which the posts are glued into the bores, can be such that a portion of the posts protrude beyond the tissue-engaging surface of the jaw so the posts are operative as gap setters.

As alluded to above, in the illustrated embodiment, once the gap setter 315 is passed across the outer surface 322, toward the tissue-engaging surface 318a, and is disposed in the bore 320 at its desired location, to the extent it is not already secure, the gap setter 315 can be secured with respect to the bore 320 using any number of techniques. In some embodiments, some form of filler or filler material (not shown) can be used to fill the bore 320 and substantially prevent movement of the gap setter 315 with respect to the bore 320. More specifically, the filler can apply a force to the gap setter 315 to substantially maintain a location of the gap setter 315 with respect to the bore 320 and the tissue engaging surface 318a of the upper jaw 316a. In the illustrated embodiment of FIGS. 6A-8, the force applied by the filler is in a direction toward the tissue engaging surface 318a. The remainder of the space in the bore 320 can be overmolded, filled with adhesive, or include another type of filler known to one having ordinary skill in the art. The amount of filler to be used can vary but should typically be sufficient to maintain the location of the gap setters 315 relative to the tissue engaging surface 318a of the upper jaw 316a. In an alternate embodiment, the force exerted on a gap setters 315 can point in any direction that would secure the gap setters 315 in place relative to the tissue engaging surface 318a, as can be appreciated by one having ordinary skill in the art.

The upper jaw 316a can be configured to have multiple bores 320 therein. In an exemplary embodiment, each of the bores 320 can be formed by drilling in the same direction from either the outer surface 322 or the tissue engagement surface 318a. All of the bores 320 can have the same lengths, different lengths, the same methods, and/or different methods for having a gap setter or a post disposed therein.

In other embodiments, the device can have multiple gap setters disposed in a bore. A bore that supports multiple gap setters can hold the gap setters in a line across their diameters, stack the gap setters along a length of the bore, or by any other means appreciated in the art. Gap setters disposed within a single bore can contact one another or include a partition between adjacent gap setters. Multiple gap setters can remain disposed in a single bore using filler material or via forces that one gap setter exert upon another gap setter that maintains their location with respect to the tissue engaging surface. By way of further non-limiting example, the gap setters can also be integrally secured to the jaw, affixed to the jaw by gluing, and/or associated with the jaw using any techniques for securing a location of one object with respect to another without departing from the spirit of the present disclosure.

Exemplary Surgical Methods

The devices provided for in the present disclosure can be used in conjunction with any surgical procedure in which tissue or the like is grasped, including but not limited to procedures in which tissue is grasped, procedures in which tissue is grasped and transected, and procedures in which tissue is grasped, transected, and sealed using applied energy. As will be appreciated, while reference is made below to particular features of a device for performing the surgical procedure, the devices can include any combination of the features described above. A person skilled in the art will further appreciate that the procedure can be a minimally invasive procedure or an open surgical procedure. The devices herein can also be used for robotic-assisted minimally invasive or open procedures. The procedure usually begins by preparing the patient for surgery and making one or more appropriately sized incisions at a desired location. In a minimally invasive procedure, one or more cannulas or trocars (not shown) can be positioned in the incisions to provide access to the surgical. One or more viewing devices, e.g., scopes, can be placed in one of the incisions to allow medical personnel to view the surgical site from outside the body.

In use, once the patient is prepared for surgery, a surgical device can be inserted through the incision and/or through the cannula and the end effector can be positioned adjacent to a desired tissue to be treated. In the open configuration, no force is imparted on the tissue engaging surfaces 18a, 18b of the upper and lower jaws 16a, 16b. The tissue to be sealed is placed between the jaws 16a,16b such that the tissue is in contact with at least one of the tissue engaging surfaces of the jaws 16a, 16b. In some instances, the tissue to be treated can include one or more layers of blood vessels. As the surgical device is being inserted into the patient, the closure actuator can be disposed adjacent to the stationary handle in which the jaws 16a, 16b are in a closed position so that the jaws 16a, 16b have a smaller width that can be inserted into a small access channel. When the jaws 16a, 16b are positioned adjacent to the tissue to be treated, the closure grip 20 can be moved away from the stationary grip 22 and the tissue to be treated can be positioned between the jaws 16a. 16b. Movement of the closure grip 20 toward the stationary grip 22 can close the jaws 16a, 16b so that tissue is securely grasped between the jaws 16a, 16b.

Actuation of the instrument causes the jaws 16a, 16b to pivot about the pivot point until the jaws 16a, 16b are in the closed configuration. In the closed configuration, the tissue engaging surfaces 18a, 18b of the jaws 16a, 16b compress the tissue disposed therebetween such that the tissue can be safely transected and/or sealed. In embodiments in which transection is to occur, after the jaws 16a, 16b are initially closed, the cutting element can remain at its proximal location. In embodiments in which the tissue or vessel is being sealed prior to being cut, the cutting element can typically remain proximate to the proximal location so that cutting is not performed until after the sealing has at least started, or until it is completed. Additionally, in the closed configuration, the gap setter 15 can come into contact with at least a portion of the opposite jaw 16b, thereby applying a force to the tissue engaging surface 18b of the opposite jaw. The presence of the gap setter 15 between the jaws 16a, 16b thereby creates a uniform gap or buffer between the jaws. This uniform gap also electrically insulates the upper jaw 16a from the electrode 17 in the opposite jaw 18b, which helps eliminate erosion of insulator material on the tissue engaging surface 18b of the jaw 16b.

The tissue can be sealed by energy supplied though the electrode 17, which can be activated and operated by one or more features incorporated into the handle assembly. For example, the firing trigger 24 can be operated to supply electrical energy to the electrode 17, and thus to the tissue grasped by the jaws 16a, 16b. The electrical energy can help weld or otherwise seal the tissue.

After energy has been delivered to the clamped tissue to seal it, and any cutting or transecting of the tissue has also occurred (either before or after the sealing), the procedure can be repeated, for instance on adjacent tissue. Thus, upon completion of the first delivery of energy (and any cutting or transecting), the jaws 16a, 16b can be moved apart to release the treated tissue and additional tissue can be clamped. Like the first instance, the clamping of the tissue can result in the jaw 116b applying a force to one or more of the gap setters 15 disposed in the jaw 16a as the jaws close. As a result, a gap or buffer is formed between the two jaws 16a, 16b. Provided the tissue is not too thick so as to impact a size of the gap, a size of the gap in the first clamping step is uniform to the size of the gap in the second (and subsequent) clamping steps. It would be uniform if no tissue was disposed in the jaws 16a, 16b. Once the tissue is grasped and the jaws 16a, 16b are in the closed configuration, energy can be delivered to the electrode 17 to seal the clamped tissue, any cutting or transecting can be performed (either before or after the sealing), and the jaws 16a, 16b can be returned toward their open configuration to release the treated tissue.

The surgical device can be inserted into the body using the method described above, but can also apply energy, e.g., RF current, to tissue disposed between the jaws prior to, during, and/or after transection of the tissue. After the cutting member is advanced through the tissue and is retracted proximally, the device 100 can continue to apply energy to the cut tissue or the jaws 16a, 16b can automatically release the tissue. In either example, after the cutting is complete, the actuator portion 10, the closure grip 20, and the jaws 16a, 16b can release from the compressed/closed positions and can automatically return to their initial position so that jaw closure, tissue compression, cutting, and/or sealing can be repeated as many times as desired. In some instances, tissue can be pulsed after the tissue has been sealed and/or cut as the cutting member is retracted proximally at the end of a firing stroke.

Additionally, after the tissue is sealed, a cutting stroke can be performed by distally advancing the cutting element through at least a portion of the jaws 16a, 16b to cut the tissue disposed between the jaws 16a, 16b. In embodiments in which the device 100 is not configured to seal tissue, the cutting element can be advanced distally any time after the jaws 16a, 16b are closed. While configurations in which a cutting mechanism is used to also close a jaw assembly are known to those in the art, some non-limiting exemplary embodiments of such a configuration are provided for in U.S. Pat. Pub. No. 2015/0190191 entitled "Electrosurgical Sealing and Transecting Devices and Methods with Improved Application of Compressive Force," which was filed on Jan. 7, 2014, the content of which is incorporated by reference herein in its entirety.

The devices disclosed herein can be designed to be disposed of after a single use, or they can be designed to be used multiple times. After the tissue has been sealed and/or transected, the cutting element assembly can be retracted and the upper and lower jaws can be moved to the open configuration. Once in the open configuration, the device can be reactuated by placing another piece of tissue between the tissue engaging surfaces of the upper and lower jaws. The process outlined above is then repeated. When the instrument is actuated and the jaws are in the closed configuration, another buffer is created. The resultant buffer formed between the jaws generally has a consistent size with the buffer discussed above. Further, in all subsequent actuations of the instrument, the buffer created between the jaws in the fully compressed configuration has a consistent size.

Whether the devices disclosed herein are used multiple times, they can be reconditioned for reuse after at least one use. Reconditioning can include any combination of the steps of disassembly of the device, followed by Cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is Obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam. One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
 a first jaw having a first tissue engaging surface, the first tissue engaging surface including an electrode;
 a second jaw pivotally coupled to the first jaw, the second jaw having a second tissue engaging surface that faces and is opposed to the first tissue engaging surface, a first bore formed in a distal portion thereof, and a second bore formed in a proximal portion thereof, each of the first and second bores extending from the second tissue engaging surface and toward an outer surface of the second jaw that is opposed to the second tissue engaging surface;
 a first electrically insulative stop disposed in the first bore of the second jaw such that a portion of the first electrically insulative stop protrudes from the second tissue engaging surface; and
 a second electrically insulative stop disposed in the second bore of the second jaw such that a portion of the second electrically insulative stop protrudes from the second tissue engaging surface,
 wherein the first and second electrically insulative stops are configured to maintain the first tissue engaging surface at a consistent distance away from the second tissue engaging surface whenever the first and second jaws are in a fully compressed configuration in which at least one of the first and second jaws applies a force to the respective first or second tissue engaging surface of the other of the first and second jaws, the first bore has a variable diameter along its length, the first bore has a diameter along its length that is less than a diameter of the first electrically insulative stop and that is closer to the outer surface of the second jaw than to the second tissue engaging surface of the second jaw, and wherein the second jaw is electrically isolated from the electrode of the first jaw in the fully compressed configuration.

2. The device of claim 1, further comprising a third electrically insulative stop disposed in a third bore formed in the proximal portion of the second jaw such that a portion of the third electrically insulative stop protrudes from the second tissue engaging surface, the third bore extending from the second tissue engaging surface and toward the outer surface of the second jaw.

3. The device of claim 2, wherein the second bore and the second electrically insulative stop are disposed on one side of a central longitudinal axis of the second jaw and the third bore and the third electrically insulative stop are disposed on an opposite side of the central longitudinal axis of the second jaw, and the second and third electrically insulative stops are aligned such that a horizontal axis extending between centers of the second and third electrically insulative stops is approximately perpendicular to the central longitudinal axis of the second jaw.

4. The device of claim 1, wherein at least one of the first and second bores extends from the second tissue engaging surface to the outer surface of the second jaw, with a diameter of the at least one of the first and second bores proximate to the second tissue engaging surface being less than a diameter of the same bore located proximate to the outer surface.

5. The device of claim 4, wherein the respective first or second electrically insulative stop disposed in the at least one of the first and second bores that extends from the second tissue engaging surface to the outer surface of the second jaw is a bead having a central diameter that is greater than the diameter of the bore in which the bead is disposed at the second tissue engaging surface and less than the diameter of the same bore at the outer surface, and wherein the device further comprises filler disposed in the bore, the filler being configured to apply force to the bead in a direction toward the second tissue engaging surface to maintain a location of the bead with respect to the second tissue engaging surface.

6. The device of claim 4, wherein both the first and the second bores extend from the second tissue engaging surface to the outer surface of the second jaw, with a diameter of each bore proximate to the second tissue engaging surface being less than a diameter of the same bore located proximate to the outer surface.

7. The device of claim 6, wherein the first electrically insulative stop is a first bead having a central diameter that is greater than the diameter of the first bore at the second tissue engaging surface and less than the diameter of the first bore at the outer surface, wherein the second electrically insulative stop is a second bead having a central diameter that is greater than the diameter of the second bore at the second tissue engaging surface and less than the diameter of the second bore at the outer surface, and wherein the device further comprises:

first filler disposed in the first bore, the first filler being configured to apply force to the first bead in a direction toward the second tissue engaging surface to maintain a location of the first bead with respect to the second tissue engaging surface; and second filler disposed in the second bore, the second filler being configured to apply force to the second bead in a direction toward the second tissue engaging surface to maintain a location of the second bead with respect to the second tissue engaging surface.

8. The device of claim 1, wherein at least one of the first and second bores terminates prior to the outer surface, the at least one of the first and second bores that terminates prior to the outer surface including an end wall that is opposed to the second tissue engaging surface, and wherein a distance between the end wall and the second tissue engaging surface is less than a length of the respective first or second electrically insulative stop disposed in the at least one of the first and second bores that terminates prior to the outer surface measured along a length of the bore such that the electrically insulative stop protrudes from the second tissue engaging surface.

9. The device of claim 1, wherein at least one of the first and second electrically insulative stops comprises glass or ceramic.

10. The device of claim 1, wherein the first and second jaws are bipolar.

11. The device of claim 1, wherein the portion of the first electrically insulative stop protrudes from the second tissue engaging surface by an amount in a range of about 0.1 mm to about 5 mm, and wherein the portion of the second electrically insulative stop protrudes from the second tissue engaging surface by an amount in a range of about 0.1 mm to about 5 mm.

12. A surgical device, comprising:

an end effector comprising a first jaw with a first tissue engaging surface and a second jaw with a second tissue engaging surface, the first and second jaws being pivotably coupled, the first tissue engaging surface including an electrode, the second tissue engaging surface being opposed to the first tissue engaging surface, and the second jaw having formed therein a plurality of bores each extending from the second tissue engaging surface and toward an outer surface of the second jaw that is opposed to the second tissue engaging surface;

at least one electrically insulative stop disposed in at least one of the plurality of bores formed in the second jaw, at least one other of the plurality of bores not having an electrically insulative stop disposed therein;

an actuator operably connected to the end effector to move the end effector between an open configuration, in which neither of the first and second jaws applies a force to the respective first or second tissue engaging surface of the other of the first and second jaws, and a fully compressed configuration, in which at least one of the first and second jaws applies a force to the respective first or second tissue engaging surface of the other of the first and second jaws; and a driver configured to deliver energy to the electrode to seal tissue disposed between the first and second jaws when the end effector is in the fully compressed configuration, wherein whenever the end effector is in the fully compressed configuration, the at least one electrically insulative stop disposed in the at least one of the plurality of bores is engaged with the first tissue engaging surface, the second jaw is electrically isolated from the electrode of the first jaw, and a gap formed between the first and second jaws has a consistent size;

wherein the at least one of the plurality of bores has a variable diameter along its length; and wherein the at least one of the plurality of bores has a diameter along its length that is less than a diameter of the at least one electrically insulative stop disposed therein and that is closer to the outer surface of the second jaw than to the second tissue engaging surface of the second jaw.

13. The device of claim 12,
wherein the at least one electrically insulative stop includes a plurality of electrically insulative stops all disposed in a single one of the plurality of bores formed in the second jaw, with at least one, but not all, of the plurality of electrically insulative stops protruding from the second tissue engaging surface.

14. The device of claim 12,
wherein the plurality of bores comprise a first bore formed in a distal portion of the second jaw, a second bore formed in a proximal portion of the second jaw, and a third bore, and
wherein the at least one electrically insulative stop comprises a first electrically insulative stop disposed in the first bore and a second electrically insulative stop disposed in the second bore.

15. The device of claim 14,
wherein the plurality of bores further comprise a fourth bore formed in the proximal portion of the second jaw, the second and fourth bores being disposed on opposite sides of a central longitudinal axis of the second jaw, and
wherein the at least one electrically insulative stop further comprises a third electrically insulative stop disposed in the fourth bore, the second and third electrically insulative stops being aligned such that a horizontal axis extending between centers of the second and third electrically insulative stops is approximately perpendicular to the central longitudinal axis of the second jaw.

16. The device of claim 12, wherein the at least one electrically insulative stop comprises a glass or ceramic bead.

17. The device of claim 12, wherein the end effector is bipolar.

* * * * *